United States Patent
Bhogu

(10) Patent No.: US 12,109,029 B2
(45) Date of Patent: Oct. 8, 2024

(54) WIRELESS CARDIAC MONITORING DEVICE AND METHOD TO MEASURE AND TRANSMIT CARDIAC PHYSIOLOGICAL SIGNALS

(71) Applicant: Monitra Healthcare Private Limited, Telangana (IN)

(72) Inventor: Ravi Bhogu, Telangana (IN)

(73) Assignee: MONITRA HEALTHCARE PRIVATE LIMITED, Telangana (IN)

( * ) Notice: Subject to any disclaimer, the term of this patent is extended or adjusted under 35 U.S.C. 154(b) by 782 days.

(21) Appl. No.: 17/232,394

(22) Filed: Apr. 16, 2021

(65) Prior Publication Data

US 2021/0228133 A1 Jul. 29, 2021

Related U.S. Application Data

(63) Continuation-in-part of application No. 15/572,432, filed as application No. PCT/IB2016/052694 on May 11, 2016, now abandoned.

(30) Foreign Application Priority Data

May 12, 2015 (IN) ............ 2418/CHE/2015

(51) Int. Cl.
*A61B 5/28* (2021.01)
*A61B 5/00* (2006.01)
(Continued)

(52) U.S. Cl.
CPC ............ *A61B 5/257* (2021.01); *A61B 5/0006* (2013.01); *A61B 5/28* (2021.01); *A61B 5/341* (2021.01);
(Continued)

(58) Field of Classification Search
CPC ..... A61B 5/0006; A61B 5/002; A61B 5/0022; A61B 5/0002; A61B 5/04017;
(Continued)

(56) References Cited

U.S. PATENT DOCUMENTS

2011/0063105 A1* 3/2011 Bennett ............... H04W 4/90
340/539.11
2013/0278414 A1* 10/2013 Sprigg ............... A61B 5/746
340/539.12

(Continued)

FOREIGN PATENT DOCUMENTS

IN 2716/DEL/2013 3/2015

OTHER PUBLICATIONS

International Search Report and Writen Opinion dated Sep. 15, 2016 for PCT application No. PCT/IB2019/052694.

*Primary Examiner* — Adam Z Minchella
(74) *Attorney, Agent, or Firm* — Ohlandt, Greeley and Perle, L.L.P.

(57) ABSTRACT

A method and a wireless cardiac monitoring device to measure and transmit cardiac physiological signals of a subject. The device comprises a patch configured to be in contact with a skin surface of the subject. The patch comprises a plurality of electrodes and at least one wire-free module, embedded in the patch. The wire-free module comprises a patch orientation detection module to detect an orientation of the patch on the subject using a plurality of sensors. The wire-free module also comprises a processing module to select at least two pair of electrodes from the plurality of electrodes based on the detected orientation of the patch and process one or more bio-potential signals corresponding to the at least two pair of electrodes selected, as the physiological signals. The wire-free module further (Continued)

comprises a transmission module to transmit the physiological signals to an external device for further processing.

15 Claims, 5 Drawing Sheets

(51) Int. Cl.
    *A61B 5/257*     (2021.01)
    *A61B 5/341*     (2021.01)
    *A61B 5/353*     (2021.01)
    *A61B 5/358*     (2021.01)

(52) U.S. Cl.
    CPC .............. *A61B 5/353* (2021.01); *A61B 5/358* (2021.01); *A61B 5/6833* (2013.01); *A61B 2562/0219* (2013.01); *A61B 2562/0223* (2013.01)

(58) Field of Classification Search
    CPC . A61B 5/04085; A61B 5/7267; A61B 5/7264; A61B 5/0404; A61B 5/04087; A61B 5/0478; A61B 5/04884; A61B 5/04886; A61B 5/0492; A61B 5/0496; A61B 5/067; A61B 5/684; A61B 5/6833; A61B 2560/0412; A61B 2562/0209; A61B 2562/0219; A61B 2562/0223
    See application file for complete search history.

(56) References Cited

U.S. PATENT DOCUMENTS

| | | | | |
|---|---|---|---|---|
| 2013/0338448 | A1* | 12/2013 | Libbus | A61B 5/061 600/509 |
| 2015/0073231 | A1* | 3/2015 | Beck | A61B 5/0006 600/301 |
| 2015/0073717 | A1 | 3/2015 | Hsu | |
| 2015/0351690 | A1* | 12/2015 | Toth | A61B 5/14542 600/391 |
| 2016/0262646 | A1* | 9/2016 | Bardy | A61B 5/333 |
| 2017/0185737 | A1* | 6/2017 | Kovacs | A61B 5/02416 |

* cited by examiner

WIRELESS CARDIAC MONITORING DEVICE AND METHOD TO MEASURE AND TRANSMIT CARDIAC PHYSIOLOGICAL SIGNALS

CROSS-REFERENCED APPLICATIONS

This application is a Continuation-in-Part of U.S. patent application Ser. No. 15/572,432 filed on Nov. 7, 2017, which claims priority to PCT Application No. PCT/IB2016/052694, filed on May 11, 2016 and Indian Patent Application No. 2418/CHE/2015 filed on May 12, 2015, all of which are incorporated herein in their entireties by reference thereto.

TECHNICAL FIELD

Embodiments of the present disclosure are related, in general to health monitoring, but exclusively relate to a method and a wireless cardiac monitoring device to measure and transmit cardiac physiological signals of a subject.

BACKGROUND

An electrocardiogram (ECG) interpretation has been the basis of observing abnormalities in cardio-vascular system or prediction of cardiovascular disease. However, the administration of ECG testing has been limited largely to diagnostic clinics, hospitals, emergency rooms and recently to remote cardiac monitoring devices. Although the benefit of remote cardiac monitoring device is significant, patient compliance remains a big challenge and these devices are prone to lead placement errors.

The common areas of noncompliance with ambulatory monitoring include the unwillingness to wear a device continuously, intolerance of the electrodes because of rash, failure to activate a monitor in association with symptoms, and inability to trans-telephonically download the information.

Accordingly, a need exists for a device for monitoring multiple ECG signals without wires to improve patient compliance, which also automatically recognizes the device orientation thereby capturing ECG signals correctly without user intervention to eliminate incorrect lead placement errors, which also records, and monitors ECG signals in real time.

SUMMARY

The shortcomings of the prior art are overcome and additional advantages are provided through the provision of method of the present disclosure.

Additional features and advantages are realized through the techniques of the present disclosure. Other embodiments and aspects of the disclosure are described in detail herein and are considered a part of the claimed disclosure.

In an aspect of the present disclosure, a wireless cardiac monitoring device to measure and transmit cardiac physiological signals of a subject is provided. The device comprises a patch configured to be in contact with a skin surface of the subject. The patch comprises a plurality of electrodes capable of generating one or more bio-potential signals therefrom. The patch also comprises at least one wire-free module, embedded in the patch. The wire-free module comprises a patch orientation detection module to detect an orientation of the patch on the subject using a plurality of sensors. The wire-free module also comprises a processing module to select at least two pair of electrodes from the plurality of electrodes based on the detected orientation of the patch and process one or more bio-potential signals corresponding to the at least two pair of electrodes selected, as the physiological signals. The wire-free module further comprises a transmission module to transmit the physiological signals to an external device for further processing.

Another aspect of the present disclosure relates to a method of measuring and transmitting physiological cardiac signals of a subject. The method comprises placing a patch comprising a plurality of electrodes, on a skin surface of the subject, to measure the physiological signals of the subject. The method further comprises detecting an orientation of the patch on the subject using a plurality of sensors. The method also comprises selecting at least two pair of electrodes from the plurality of electrodes based on the detected orientation of the patch, and processing one or more bio-potential signals corresponding to the at least two pair of electrodes selected, as the physiological signals. The method further comprises transmitting the physiological signals to an external device for further processing.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of device or system and/or methods in accordance with embodiments of the present subject matter are now described, by way of example only, and with reference to the accompanying figures, in which.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

Figure 1A:
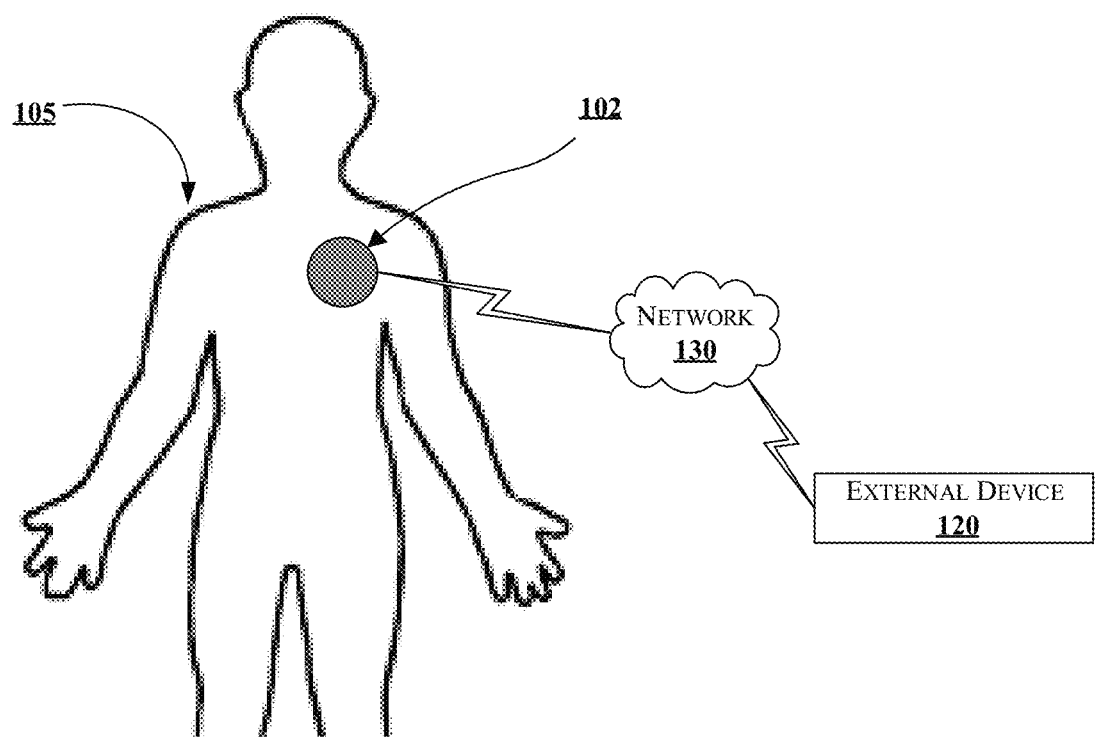
FIG. 1A illustrates an exemplary architecture of a cardiac monitoring system in accordance with embodiments of the present disclosure.

FIG. 1A illustrates an exemplary architecture of a cardiac monitoring system in accordance with embodiments of the present disclosure.

As illustrated in FIG. 1A, the exemplary architecture of a cardiac monitoring system 100 comprises a patch 102 placed in contact with a skin surface of a subject 105, and an external device 120 communicatively coupled via a network 130. The network 130 may be a LAN (local area network), WAN (wide area network), wireless network, cellular network, point-to-point network, or another configuration.

The patch 102 measures one or more physiological signals from the subject 105 and wirelessly transmits the one or more physiological signals to the external device 120 via the network 130.

In one embodiment, the external device 120 receives the one or more physiological signals, analyses and processes the one or more physiological signals. The external device 120 process the one or more physiological signals to determine ECG signals, wherein the ECG signals give information about the electrical function of the heart. From the ECG signals, the external device 120 predicts abnormalities related to cardio-vascular system.

The external device 120 may be a mobile device or a computing device including the functionality for communicating over the network 130. For example, the external device 120 can be a conventional web-enabled personal computer in the home, mobile computer (laptop, notebook or subnotebook), Smart Phone with any operating system such as iOS or Android, personal digital assistant, wireless electronic mail device, tablet computer or other device capable of communicating both ways over the Internet or other appropriate communications network. The external device 120 may comprise an integrated software application with a user interface that enables interaction with the patch 102.

Figure 1B:
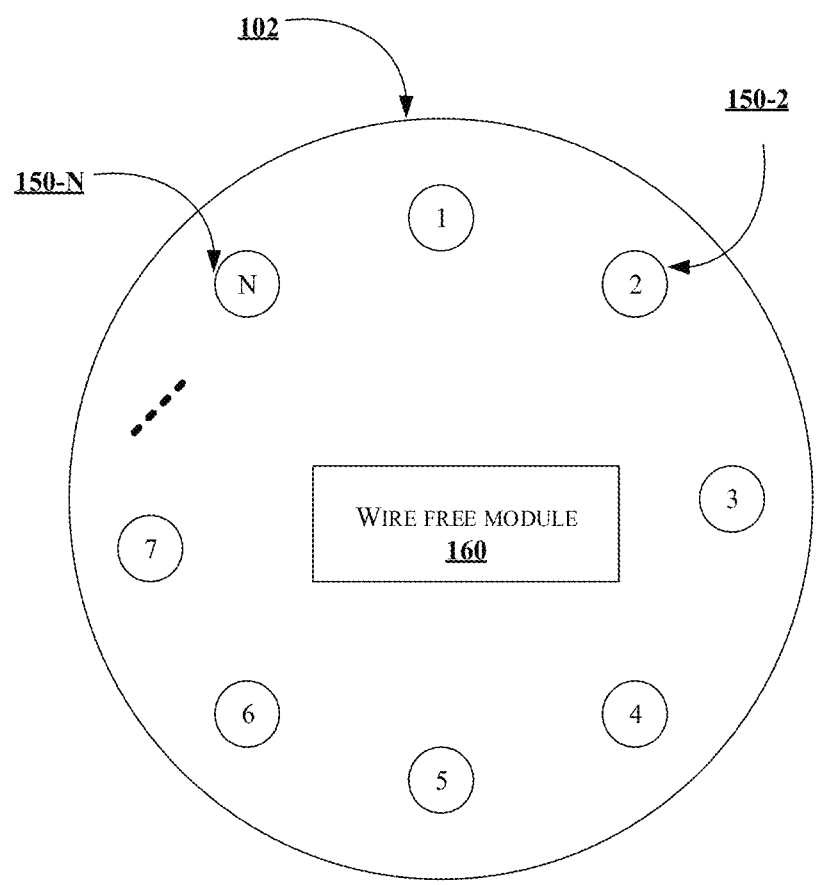
FIG. 1B illustrates an exemplary patch of the cardiac monitoring system in accordance with embodiments of the present disclosure.

FIG. 1B illustrates an exemplary patch of the cardiac monitoring system in accordance with embodiments of the present disclosure.

As illustrated in FIG. 1B, the patch 102 comprises a plurality of electrodes 150-1, 150-2, . . . 150-N (collectively referred to as 150) and a wire-free module 160 communicatively coupled to the plurality of electrodes 150. The plurality of electrodes 150 placed on the skin of the subject 105 measures bio-potential signals of the subject 105 The wire-free module 160 is configured to detect orientation of the patch 102 on the subject and select at least two pair of electrodes from the plurality of electrodes 150. The wire-free module 160 is then configured to measure the one or more bio-potential signals corresponding to selected at least two pair of electrodes and transmit to the external device 120 as one or more physiological signals.

Figure 2:
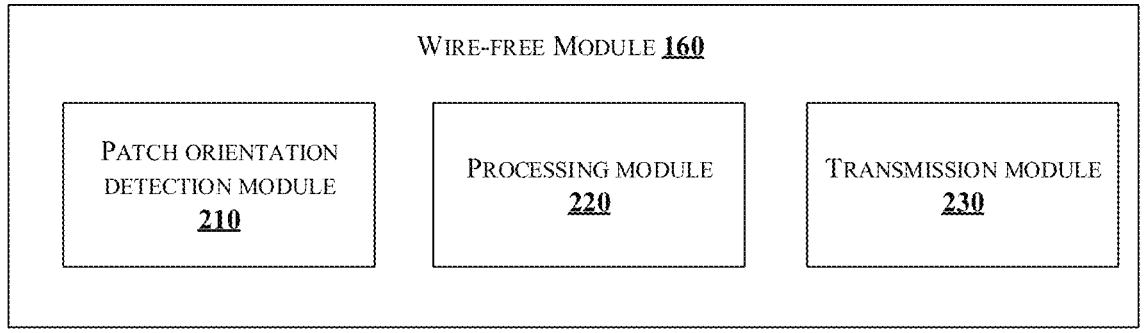
FIG. 2 illustrates a block diagram illustrating wire-free module of FIG. 1B in accordance with embodiments of the present disclosure.

FIG. 2 shows a block diagram illustrating the wire-free module of FIG. 1B in accordance with some embodiments of the present disclosure.

In an implementation, the wire-free module 160 may include one or more modules such as patch orientation detection module 210, processing module 220, and a transmission module 230.

The patch orientation detection module 210 is configured to detect orientation of the patch 102 placed on the subject 105. The patch orientation detection module comprises a plurality of sensors to detect the orientation of the patch 102. The plurality of sensors include, but not limited to, accelerometer sensor, gyroscope sensor, and magneto sensor.

The processing module 220 is coupled to the patch orientation detection module 210. The processing module 220 is configured to receive orientation information of the patch 102 from the patch orientation detection module 210. Based on the detected orientation of the patch 102, the processing module 220 is configured to select at least two pair of electrodes from the plurality of electrodes 150.

In order to select at least two pair of electrodes, the processing module 220 is configured to initially select a subset of electrodes from the plurality of electrodes 150 based on the detected orientation. In one aspect, the subset of electrodes to be selected for each orientation of the patch 102 are predefined and calibrated during the manufacturing process. The processing module 220 is then configured to correlate each of a vector connecting at least two electrodes of the subset of electrodes with a reference axis. The reference axis can be either one of horizontal axis, vertical axis. For correlating each of the vector with the reference axis, the processing module 220 is configured to determine an angular distance between each of the vector and the reference axis and then estimate an inter-electrode distance for each of the vector. Based on the determined angular distance and the inter-electrode distance, the processing module 220 determines confidence score for each of the vector. The processing module select the at least two pair of electrodes based on the confidence score determined. For example, when there are one or more vectors which are parallel to the reference axis, then the processing module 220 selects a pair of electrodes having highest inter-electrode distance.

In one embodiment, when the reference axis is horizontal axis, the processing module 220 correlates each of the vector connecting at least two electrodes with the horizontal axis. The processing module 220 then select a first pair of electrode based on the correlation. The processing module 220 further process the bio-potential signals from the selected first pair of electrodes, as the Lead I signal. In another embodiment, when the reference axis is vertical axis, the processing module 220 correlates each of the vector connecting at least two electrodes with the vertical axis. The processing module 220 then select a second pair of electrode based on the correlation. The processing module 220 further process the bio-potential signals from the selected second pair of electrodes, as the Lead III signal.

The processing module 220 is then configured to determine Lead II based on the Lead I and Lead III signal, as the Lead II signal is equal to combination of Lead I and Lead III signals.

The transmission module 230 is coupled to the processing module 220. After the processing module 220 measures the physiological signals such as Lead I, II, III signals, the transmission module 230 is configured to transmit the physiological signals to the external device 120 for further processing.

Figure 3:
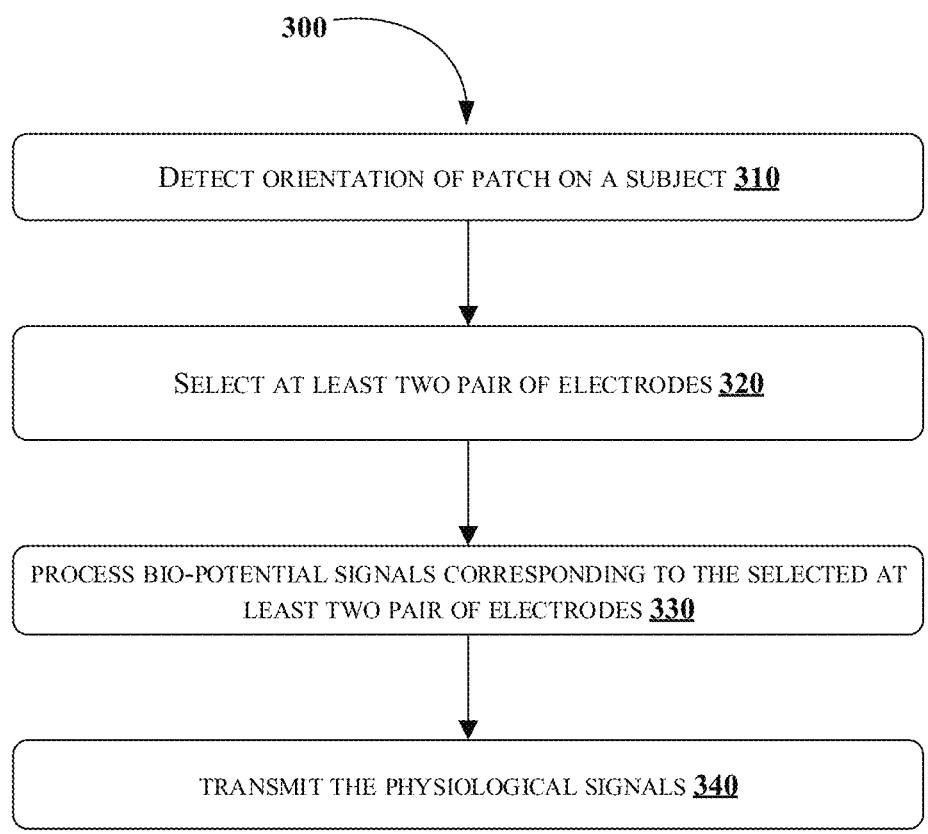
FIG. 3 illustrates exemplary steps of a method performed by wire-free module in accordance with embodiments of the present disclosure.

FIG. 3 illustrates exemplary steps of a method performed by wire-free module in accordance with embodiments of the present disclosure. As illustrated in FIG. 3, the method comprises one or more steps implemented by wire-free module. The method may be described in the general context of computer executable instructions. Generally, computer executable instructions can include routine, programs, objects, components, data structures, procedures, units, and functions, which perform particular functions or implement particular abstract data types.

At step 310, an orientation of patch on a subject 105 is detected. In one embodiment, the patch orientation detection module 210 is configured to detect orientation of the patch 102 placed on the subject 105. The patch orientation detection module 210 comprises a plurality of sensors to detect the orientation of the patch 102. The plurality of sensors includes, but not limited to, accelerometer sensor, gyroscope sensor, and magneto sensor.

At step 320, at least two pair of electrodes is selected. The processing modules 220 is configured to receive orientation information of the patch 102 from the patch orientation detection module 210. Based on the detection orientation of the patch 102, the processing module 220 is configured to select at least two pair of electrodes from the plurality of electrodes 150. In order to select at least two pair of electrodes, the processing module 220 is configured to initially select a subset of electrodes from the plurality of electrodes 150 based on the detected orientation. The processing module 220 is then configured to correlate each of a vector connecting at least two electrodes of the subset of electrodes with a reference axis. The reference axis can be either one of horizontal axis, vertical axis.

For correlating each of the vector with the reference axis, the processing module 220 is configured to determine an angular distance between each of the vector and the reference axis and then estimate an inter-electrode distance for each of the vector. Based on the determined angular distance and the inter-electrode distance, the processing module 220 determines confidence score for each of the vector. The processing module 220 select the at least two pair of electrodes based on the confidence score determined. In one embodiment, when one or more vectors have same angular distance and inter-electrode distance, the processing module 220 then determines an amplitude of a signal corresponding to a pair of electrodes included in each of the vector. Based on the amplitude of the signal, the processing module 220 selects the pair of electrodes.

In one embodiment, the processing module determines the amplitude of the signal by measuring P wave amplitude and QRS wave amplitude.

In one embodiment, when the reference axis is horizontal axis, the processing module 220 correlates each of the vector connecting at least two electrodes with the horizontal axis. The processing module 220 then selects a first pair of electrode based on the correlation. In another embodiment, when the reference axis is vertical axis, the processing module correlates each of the vector connecting at least two electrodes with the vertical axis. The processing module then selects a second pair of electrode based on the correlation.

At step 330, bio-potential signals corresponding to the selected at least two pair of electrodes are processed. In one embodiment, when the reference axis is horizontal axis, the processing module 220 correlates each of the vector connecting at least two electrodes with the horizontal axis. The processing module 220 then selects a first pair of electrode based on the correlation. The processing module 220 further processes the bio-potential signals from the selected first pair of electrodes, as the Lead I signal. In another embodiment, when the reference axis is vertical axis, the processing module 220 correlates each of the vector connecting at least two electrodes with the vertical axis. The processing module 220 then select a second pair of electrode based on the correlation. The processing module 220 further process the bio-potential signals from the selected second pair of electrodes, as the Lead III signal.

The processing module 220 is then configured to determine Lead II based on the Lead I and Lead III signal, as the Lead II signal is equal to combination of Lead I and Lead III signals.

At step 340, transmit the physiological signals are transmitted. After the processing module measures the physiological signals such as Lead I, II, III signals, the transmission module 230 is configured to transmit the physiological signals to the external device 120 for further processing.

Thus, the cardiac monitoring system 100 enables real time accurate measuring and transmitting physiological signals to external device even when the patch is placed in any angle without any expert guidance.

Figure 4A:
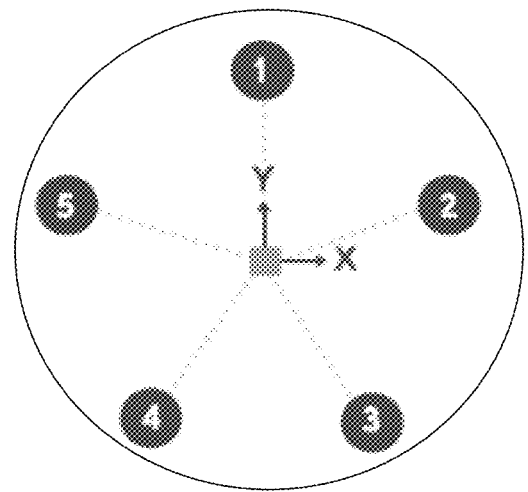
FIG. 4A illustrates an exemplary patch having five electrodes in accordance with some embodiments of the present disclosure.

FIG. 4A illustrates an exemplary patch having 5 electrodes. As illustrated, the patch 102 is placed along X-Y axis, such that the relationship between the location of the electrodes and orientation of patch is determined and calibrated at the time of manufacturing of the patch 102.

Figure 4B:
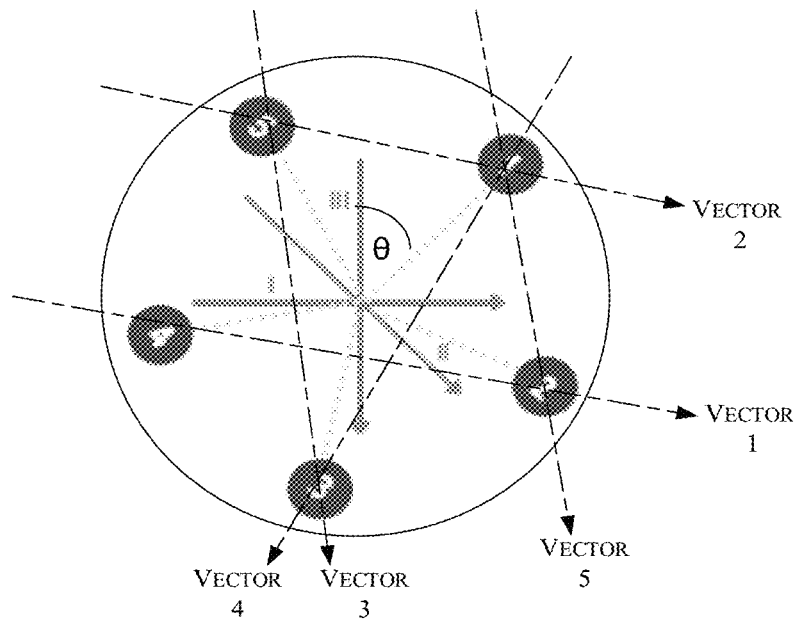
FIG. 4B illustrates the exemplary patch of the FIG. 4A when the patch is oriented by an angle θ in accordance with some embodiments of the present disclosure.

FIG. 4B illustrates the exemplary patch of the FIG. 4A when the patch is oriented by an angle θ in accordance with some embodiments of the present disclosure.

As illustrated in FIG. 4B, the patch 102 comprising five electrodes is applied on the subject 105 at angle θ. Once the patch 102 is applied on the body of the subject, the patch orientation detection module 210 of the wire-free module 160 as explained in FIG. 2 detects the orientation of the patch 102. The processing module 220 coupled to the patch orientation detection module 210 then receives orientation information of the patch 102 from the patch orientation detection module 210. Based on the detected orientation of the patch 102, the processing module 220 is configured to select a subset of electrodes. In one embodiment, the subset of electrodes are selected based on predefined mapping of location of electrodes and the detected orientation of the patch 102. The processing module 220 is then configured to correlate each of a vector connecting at least two electrodes of the subset of electrodes with a reference axis. The reference axis can be either one of horizontal axis and vertical axis.

For correlating each of the vector with the horizontal axis, the processing module 220 is initially configured to select electrodes 2 & 4 and electrodes 1 & 5. The processing module 220 then determines an angular distance between vector 1 and the horizontal axis and estimates an inter-electrode distance between electrodes 2 & 4 for vector 1, wherein the vector 1 is a line joining electrodes 2 & 4. The processing module 220 also determines an angular distance between vector 2 and the horizontal axis and estimates an inter-electrode distance between electrodes 1 & 5 for vector 2, wherein the vector 2 is a line joining electrodes 1 & 5. Based on the determined angular distance and the inter-electrode distance, the processing module 220 determines confidence score for vector 1 and vector 2, wherein the confidence score indicates probability of each vector being closely aligned to the horizontal axis. The processing module 220 then selects the vector 1 having electrodes 2 & 4 based on the high confidence score determined. Similar analysis is carried out for selecting the pair of electrodes along the vertical axis. For correlating each of the vector with the vertical axis, the processing module 220 is initially configured to select electrodes 3 & 5, electrodes 1 & 3, and electrodes 1 & 2. The processing module 220 determines an angular distance between vector 3 and the vertical axis and estimates an inter-electrode distance between electrodes 3 & 5 for vector 3, wherein the vector 3 is a line joining electrodes 3 & 5. The processing module 220 determines an angular distance between vector 4 and the vertical axis and then estimates an inter-electrode distance between electrodes 1 & 3 for vector 4, wherein the vector 4 is a line joining electrodes 1 & 3. The processing module 220 determines an angular distance between vector 5 and the vertical axis and then estimates an inter-electrode distance between electrodes 1 & 2 for vector 5, wherein the vector 5 is a line joining electrodes 1 & 2. Based on the determined angular distance and the inter-electrode distance, the processing module 220 determines confidence score for vector 3, vector 4, and vector 5, wherein the confidence score indicates probability of the each of vector is closely aligned to the vertical axis. The processing module 220 then select the vector 3 having electrodes 3 & 5 based on the high confidence score determined.

Figure 5A:
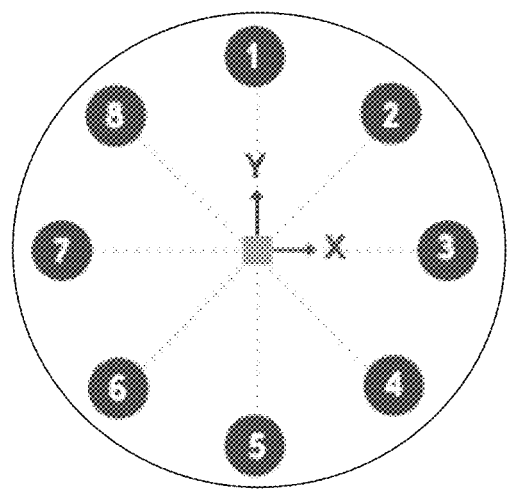
FIG. 5A illustrates an exemplary patch having eight electrodes in accordance with some embodiments of the present disclosure.

FIG. 5A illustrates an exemplary patch having 8 electrodes. As illustrated, the patch 102 is placed along X-Y axis, such that the relationship between the location of the electrodes and orientation of patch is determined and calibrated at the time of manufacturing of the patch 102.

Figure 5B:
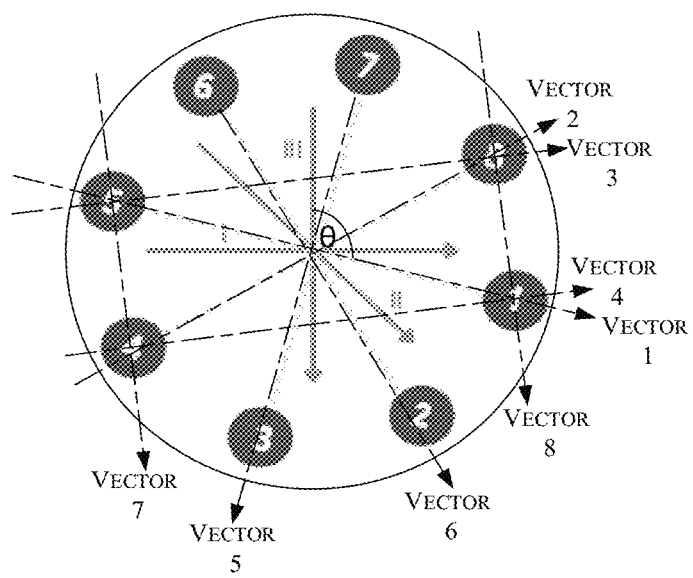
FIG. 5B illustrates the exemplary patch of the FIG. 5A when the patch is oriented by an angle θ in accordance with some embodiments of the present disclosure.

FIG. 5B illustrates the exemplary patch of the FIG. 5A when the patch is oriented by an angle $\theta$ in accordance with some embodiments of the present disclosure.

As illustrated in FIG. 5B, the patch 102 comprising eight electrodes is applied on the subject 105 at an angle $\theta$. Once the patch 102 is applied on the body of the subject, the patch orientation detection module 210 of the wire-free module 160 as explained in FIG. 2 detects the orientation of the patch 102. The processing module 220 coupled to the patch orientation detection module 210 then receives orientation information of the patch 102 from the patch orientation detection module 210. Based on the detected orientation of the patch 102, the processing module 220 is configured to select a subset of electrodes. In one embodiment, the subset of electrodes are selected based on predefined mapping of location of electrodes and the detected orientation of the patch 102. The processing module 220 is then configured to correlate each of a vector connecting at least two electrodes of the subset of electrodes with a reference axis. The reference axis can be either one of horizontal axis and vertical axis.

For correlating each of the vector with the horizontal axis, the processing module 220 is initially configured to select electrodes 1 & 5, electrodes 4 & 8, electrodes 5 & 8, and electrodes 1 & 4. The processing module 220 is then determine an angular distance between vector 1 and the horizontal axis and estimates an inter-electrode distance between electrodes 1 & 5 for vector 1, wherein the vector 1 is a line joining electrodes 1 & 5. The processing module 220 also determines an angular distance between vector 2 and the horizontal axis and estimates an inter-electrode distance between electrodes 4 & 8 for vector 2, wherein the vector 2 is a line joining electrodes 4 & 8. The processing module 220 also determines an angular distance between vector 3 and the horizontal axis and estimates an inter-electrode distance between 5 & 8 for vector 3, wherein the vector 3 is a line joining electrodes 5 & 8. The processing module 220 also determines an angular distance between vector 4 and the horizontal axis and then estimate an inter-electrode distance between electrodes 1 & 4 for vector 4, wherein the vector 4 is a line joining electrodes 1 & 4. Based on the determined angular distance and the inter-electrode distance, the processing module 220 determines confidence score for vector 1, vector 2, vector 3, and vector 4 wherein the confidence score indicates probability of the each of vector is closely aligned to the horizontal axis. The processing module 220 then selects the vector 1 having electrodes 1 & 5 based on the high confidence score determined. Similar analysis is carried out for selecting the pair of electrodes along the vertical axis.

For correlating each of the vector with the vertical axis, the processing module 220 is initially configured to select electrodes 3 & 7, electrodes 2 & 6, electrode 4 &5, and electrode 1 & 8. The processing module 220 determines an angular distance between vector 5 and the vertical axis and estimates an inter-electrode distance between 3 & 7 for vector 5, wherein the vector 5 is a line joining electrodes 3 & 7. The processing module 220 determines an angular distance between vector 6 and the vertical axis and estimates an inter-electrode distance for vector 6, wherein the vector 5 is a line joining electrodes 2 & 6. The processing module 220 determines an angular distance between vector 7 and the vertical axis and estimates an inter-electrode distance between electrodes 4 & 5 for vector 7, wherein the vector 7 is a line joining electrodes 4 & 5. The processing module 220 determines an angular distance between vector 8 and the vertical axis and estimates an inter-electrode distance between electrodes 1 & 8 for vector 8, wherein the vector 8 is a line joining electrodes 1 & 8.

Based on the determined angular distance and the inter-electrode distance, the processing module 220 determines confidence score for vector 5, vector 6, vector 7, and vector 8, wherein the confidence score indicates the probability of the each of vector is closely aligned to the vertical axis. The processing module 220 then select the vector 5 having electrodes 3 & 7 based on the high confidence score determined.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a." "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), readonly memory (ROM), volatile memory, non-volatile memory, hard drives, CD ROMs, DVDs, flash drives, disks, and any other known physical storage media.

Finally, the language used in the specification has been principally selected for readability and instructional purposes, and it may not have been selected to circumscribe the inventive subject matter. Accordingly, the disclosure of the embodiments of the disclosure is intended to be illustrative, but not limiting, of the scope of the disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

What is claimed is:

1. A wireless cardiac monitoring device to measure and transmit cardiac physiological signals of a subject, the device comprising:
    a patch configured to be in contact with a skin surface of the subject, comprising:
        a plurality of electrodes capable of generating one or more bio-potential signals therefrom; and
        at least one wire-free module, embedded in the patch, comprising:
            a patch orientation detection module to detect an orientation of the patch on the subject using a plurality of sensors;
            a processing module to:
                select at least two pair of electrodes from the plurality of electrodes based on the detected orientation of the patch by:
                    selecting a subset of electrodes from the plurality of electrodes based on the detected orientation, wherein the subset of electrodes are predefined for each detected orientation;
                    correlating one or more vectors each connecting at least two electrodes of the subset of electrodes with a reference axis, wherein the reference axis is at least one of a horizontal axis and a vertical axis;
                    determining a confidence score for each of the one or more vectors; and
                    selecting the at least two pair of electrodes based on the confidence score determined; and
                process one or more bio-potential signals corresponding to the at least two pair of electrodes selected, as the physiological signals; and
            a transmission module to transmit the physiological signals to an external device for further processing.

2. The device of claim 1, wherein to correlate the one or more vectors each connecting at least two electrodes of the subset of electrodes with the reference axis, the processing module is configured to:
    determine an angular distance between each of the one or more vectors and the reference axis; and
    estimate an inter-electrode distance for each of the one or more vectors.

3. The device of claim 2, wherein the processing module is configured to determine the confidence score for each of the one or more vectors based on the angular distance and the inter-electrode distance.

4. The device of claim 2, wherein to correlate a vector joining each of at least two electrodes of the subset of electrodes with the reference axis, the processing module is further configured to determine an amplitude of a signal corresponding to a pair of electrodes included in each of the one or more vectors.

5. The device of claim 4, wherein the processing module is configured to determine the confidence score for each of the one or more vectors based on the determined amplitude of the signal.

6. The device of claim 4, wherein the processing module is configured to measure P wave amplitude and QRS wave amplitude of the signal to determine the amplitude of the signal.

7. The device of claim 1, wherein to select the at least two pair of electrodes based on the determined confidence score, the processing module is configured to:
    select a first pair of electrodes of the at least two pair of electrodes when the reference axis is the horizontal axis; and
    select a second pair of electrodes of the at least two pair of electrodes when the reference axis is the vertical axis.

8. The device of claim 1, wherein the plurality of sensors includes at least one of an accelerometer, a gyroscope and a magnetometer.

9. A method of measuring and transmitting physiological cardiac signals of a subject, the method comprising:
    placing a patch comprising a plurality of electrodes, on a skin surface of the subject, to measure the physiological signals of the subject;
    detecting an orientation of the patch on the subject using a plurality of sensors;
    selecting at least two pair of electrodes from the plurality of electrodes based on the detected orientation of the patch by:
        selecting a subset of electrodes from the plurality of electrodes based on the detected orientation;
        correlating one or more vectors each connecting at least two electrodes of the subset of electrodes with a reference axis, wherein the reference axis is at least one of a horizontal axis and a vertical axis;
        determining a confidence score for each of the one or more vectors; and
        selecting the at least two pair of electrodes based on the confidence score determined;
    processing one or more bio-potential signals corresponding to the at least two pair of electrodes selected, as the physiological signals; and
    transmitting the physiological signals to an external device for further processing.

10. The method of claim 9, wherein correlating the one or more vectors each connecting at least two electrodes of the subset of electrodes with a reference axis includes:
    determining an angular distance between each of the one or more vectors and the reference axis; and
    estimating an inter-electrode distance for each of the one or more vectors.

11. The method of claim 10, wherein determining a confidence score for each of the one or more vectors includes determining the confidence score for each of the one or more vectors based on the angular distance and the inter-electrode distance.

12. The method of claim 10, wherein correlating a vector connecting each of at least two electrodes of the subset of electrodes with a reference axis further includes determining an amplitude of a signal corresponding to a pair of electrodes included in each of the one or more vectors.

13. The method of claim 12, wherein determining the confidence score for each of the one or more vectors further includes determining the confidence score for each of the one or more vectors based on the determined amplitude of the signal.

14. The method of claim 12, wherein the amplitude of the signal is determined based on P wave amplitude and QRS wave amplitude of the signal.

15. The method of claim 9, wherein selecting the at least two pair of electrodes based on the confidence score includes:
  selecting a first pair of electrodes of the at least two pair of electrodes when the reference axis is the horizontal axis; and
  selecting a second pair of electrodes of the at least two pair of electrodes when the reference axis is the vertical axis.

\* \* \* \* \*